US008812128B2

(12) United States Patent
Kothandaraman

(10) Patent No.: US 8,812,128 B2
(45) Date of Patent: Aug. 19, 2014

(54) IMPLANTABLE NEUROSTIMULATOR-INITIATED STATUS NOTIFICATION

(75) Inventor: Sridhar Kothandaraman, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 293 days.

(21) Appl. No.: 13/294,871

(22) Filed: Nov. 11, 2011

(65) Prior Publication Data
US 2012/0123505 A1    May 17, 2012

Related U.S. Application Data

(60) Provisional application No. 61/414,788, filed on Nov. 17, 2010.

(51) Int. Cl.
*A61N 1/37* (2006.01)
*A61N 1/372* (2006.01)
*A61N 1/378* (2006.01)

(52) U.S. Cl.
USPC .............................................. 607/60; 607/63

(58) Field of Classification Search
USPC .......................................... 607/29, 59–61, 64
See application file for complete search history.

(56) References Cited

U.S. PATENT DOCUMENTS

| | | | |
|---|---|---|---|
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,650,184 B2 | 1/2010 | Walter | |
| 8,019,439 B2 | 9/2011 | Kuzma et al. | |
| 2006/0122667 A1* | 6/2006 | Chavan et al. | 607/60 |
| 2007/0060967 A1 | 3/2007 | Strother et al. | |
| 2007/0168007 A1 | 7/2007 | Kuzma et al. | |
| 2007/0293914 A1 | 12/2007 | Woods et al. | |
| 2008/0306569 A1* | 12/2008 | Tobacman | 607/29 |
| 2009/0216306 A1 | 8/2009 | Barker | |

FOREIGN PATENT DOCUMENTS

| | | |
|---|---|---|
| WO | WO 01/54753 A2 | 8/2001 |
| WO | WO 2009/080784 A2 | 7/2009 |

OTHER PUBLICATIONS

PCT International Search Report for PCT/US2011/060449, Applicant: Boston Scientific Neuromodulation Corporation, Form PCT/ISA/210 and 220, dated Jan. 12, 2012 (5pages).
PCT Written Opinion of the International Search Authority for PCT/US2011/060449, Applicant: Boston Scientific Neuromodulation Corporation, Form PCT/ISA/237, dated Jan. 12, 2012 (7pages).

* cited by examiner

*Primary Examiner* — Allen Porter, Jr.
(74) *Attorney, Agent, or Firm* — Vista IP Law Group LLP

(57) ABSTRACT

A medical system comprises an implantable medical device having a power source, the implantable medical device configured for monitoring a quantity of the stored energy in the power source, generating a battery status signal based on the monitored quantity of stored energy, and for transcutaneously transmitting a communication initiation signal and the battery status signal. The medical system further comprises an external device configured for transcutaneously receiving the communication initial signal and the battery status signal from the rechargeable implantable medical device, changing from a relatively low energy consumption state to a relatively high energy consumption state in response to the received communication initiation signal, and for generating a user-discernible signal in response to the received status signal.

20 Claims, 5 Drawing Sheets

IMPLANTABLE NEUROSTIMULATOR-INITIATED STATUS NOTIFICATION

RELATED APPLICATION DATA

The present application claims the benefit under 35 U.S.C. §119 to U.S. provisional patent application Ser. No. 61/414,788, filed Nov. 17, 2010. The foregoing application is hereby incorporated by reference into the present application in its entirety.

FIELD OF THE INVENTION

The present invention relates to implantable devices, and more particularly, to devices for transcutaneously recharging devices implanted within patients.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

These implantable neurostimulation systems typically include one or more electrode carrying stimulation leads, which are implanted at the desired stimulation site, and an implantable pulse generator (IPG) implanted remotely from the stimulation site, but coupled either directly to the stimulation lead(s) or indirectly to the stimulation lead(s) via a lead extension. Thus, electrical pulses can be delivered from the IPG to the stimulation leads to stimulate the tissue and provide the desired efficacious therapy to the patient.

The neurostimulation system may further comprise a handheld external control device in the form of a remote control (RC) to remotely instruct the IPG to generate electrical stimulation pulses in accordance with selected stimulation parameters. A typical stimulation parameter set may include the electrodes that are acting as anodes or cathodes, as well as the amplitude, duration, and rate of the stimulation pulses. The RC may, itself, be programmed by a clinician, for example, by using a clinician's programmer (CP), which typically includes a general purpose computer, such as a laptop, with a programming software package installed thereon. Typically, the RC can only control the IPG in a limited manner (e.g., by only selecting a program or adjusting the pulse amplitude or pulse width), whereas the CP can be used to control all of the stimulation parameters, including which electrodes are cathodes or anodes. In any event, once the IPG is programmed, it is capable providing the required neurostimulation therapy to the patient without being actively linked to the RC or CP.

Of course, rechargeable medical devices, such as IPGs are active devices requiring energy for operation. Oftentimes, it is desirable to recharge an IPG via an external charger, so that a surgical procedure to replace a power depleted IPG can be avoided. To wirelessly convey energy between the external charger and the already implanted IPG, the recharger typically includes an alternating current (AC) charging coil that supplies energy to a similar charging coil located in or on the implantable pulse generator. This system is like a loosely coupled inductive transformer where the primary coil is in the external charger and the secondary coil is in the IPG. The energy received by the charging coil located on the IPG can then be used to directly power the electronic componentry contained within the IPG, or can be stored in a rechargeable battery within the IPG, which can then be used to power the electronic componentry on-demand.

Rechargeble IPGs used for applications that need continuous operation have a need to manage battery status (e.g., the remaining energy capacity of the battery, the remaining time before recharge of the battery is necessary, etc) and to ensure patient compliance with timely recharging of the IPGs. Typically, charge status information is sent from the IPG to an external control device only when the external control device prompts the IPG to do so. For example, oftentimes, the IPG will transmit charge status information to an external control device upon initial communication between these devices. However, because the external control device and IPG will not always be actively linked to each other, the battery capacity of IPG may run dangerously low or otherwise drop to a level insufficient to support continued neurostimulation therapy without ever providing a notification to the patient.

There, thus, remains a need for an improved method and system for notifying a user of the battery status of an rechargeable implantable medical device.

SUMMARY OF THE INVENTION

In accordance with a first aspect of the present inventions, an implantable medical device comprises a power source configured for storing energy, monitoring circuitry configured for monitoring a quantity of the stored energy in the power source, and control circuitry configured for generating a battery status signal based on the monitored quantity of stored energy. The battery status signal may be, e.g., an alert signal that indicates that the stored energy in the power source is below a threshold level, quantitative information indicating the remaining energy level in the power source, or quantitative information indicating the remaining operating time of the power source. In one embodiment, the power source is a rechargeable battery, in which case, the battery status signal can take the form of a battery charge status signal. In another embodiment, the power source is a non-rechargeable battery, in which case, the battery status signal can take the form of a battery end-of-life/end-of-service (EOL/EOS) status signal.

The implantable medical device further comprises telemetry circuitry configured for transcutaneously sending a communication initiation signal to an external device to initiate communication with the external device (e.g., a wake-up signal capable of prompting the external control device to change from a relatively low energy consumption state to a relatively high energy consumption state), and sending the battery status signal to the external device. The implantable medical device further comprises a housing containing the power source, the monitoring circuitry, the control circuitry, and the telemetry circuitry.

In accordance with a second aspect of the present inventions, an external device for use with a rechargeable implantable medical device having a power source is provided. The external device comprises telemetry circuitry configured for transcutaneously receiving a communication initial signal and a battery status signal from the rechargeable implantable medical device. The external device further comprises control circuitry configured for changing the external device from a relatively low energy consumption state to a relatively high energy consumption state in response to the received communication initiation signal. The external device further comprises an indicator (e.g., an audio transducer or visual display) configured for generating a user-discernible signal (e.g., an alert signal or a signal that quantitatively indicates the remaining energy level in the power source or that quantitatively indicates the remaining operating time of the power source), in response to the received status signal.

In accordance with a third aspect of the present inventions, a medical system comprises an implantable medical device (e.g., an implantable pulse generator) having a power source (e.g., a rechargeable battery, such as a lithium-ion battery), the implantable medical device configured for monitoring a quantity of the stored energy in the power source, generating a battery status signal based on the monitored quantity of stored energy, and for transcutaneously sending a communication initiation signal and the battery status signal.

The medical system further comprises an external device configured for transcutaneously receiving the communication initial signal and the battery status signal from the rechargeable implantable medical device, changing from a relatively low energy consumption state to a relatively high energy consumption state in response to the received communication initiation signal, and for generating a user-discernible signal in response to the received status signal. In one embodiment, the power source is a rechargeable battery, in which case, the battery status signal can take the form of a battery charge status signal. In another embodiment, the power source is a non-rechargeable battery, in which case, the battery status signal can take the form of a battery end-of-life/end-of-service (EOL/EOS) status signal.

In one embodiment, the battery status signal indicates that the stored energy in the power source is below a threshold level, in which case, the user-discernible signal may be an alert signal. In another embodiment, the battery status signal comprises quantitative information indicating the remaining energy level in the power source, in which case, the user-discernible signal may quantitatively indicate the remaining energy level in the power source. In still another embodiment, the battery status signal comprises quantitative information indicating the remaining operating time of the power source, in which case, the user-discernible signal may quantitatively indicate the remaining operating time of the power source.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of neurostimulation system, such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
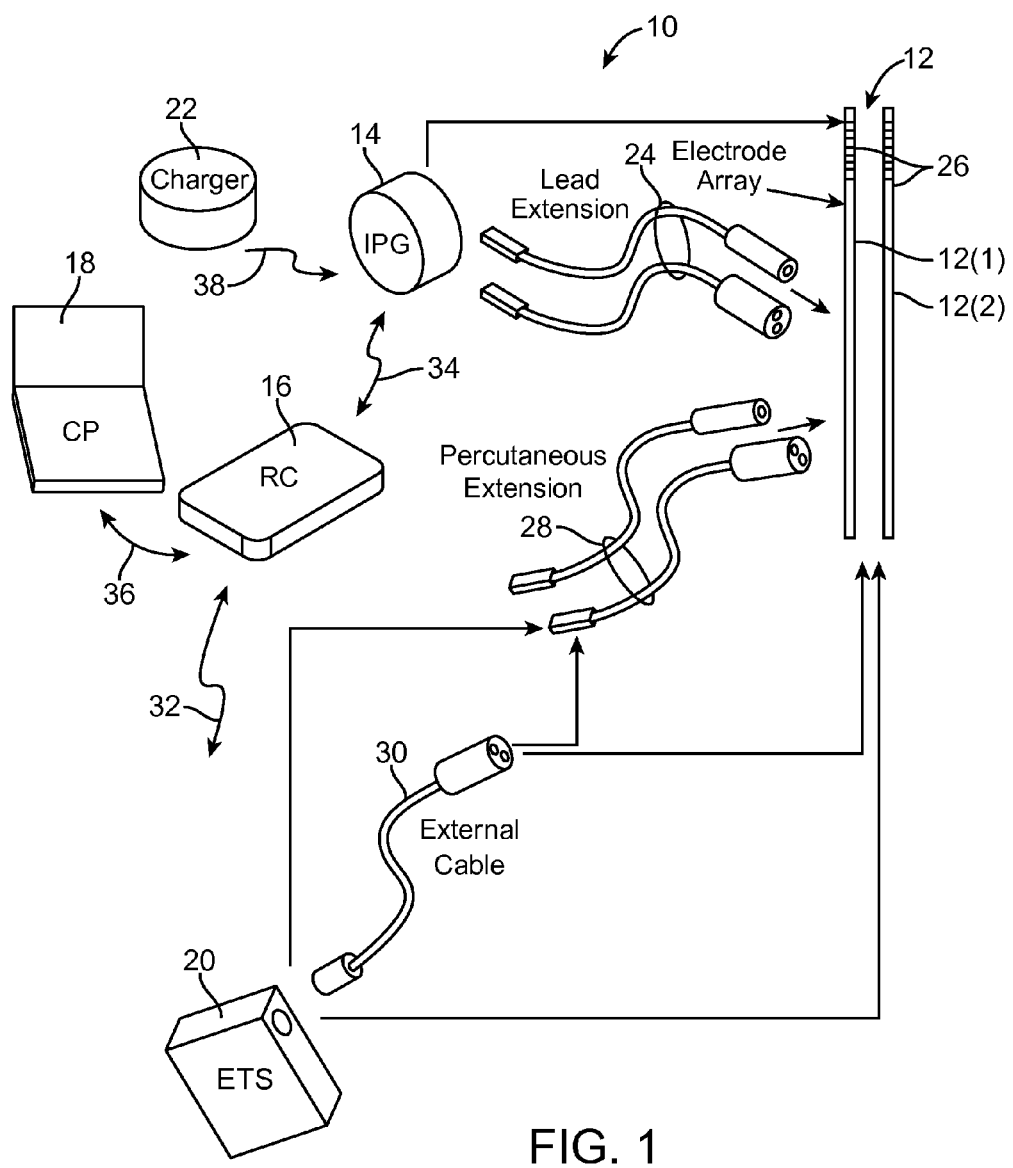
FIG. 1 is plan view of one embodiment of a spinal cord stimulation (SCS) system arranged in accordance with the present inventions.

Turning first to FIG. 1, an exemplary SCS system 10 generally comprises a plurality of percutaneous leads 12 (in this case, two percutaneous leads 12(1) and 12(2)), an implantable pulse generator (IPG) 14, an external remote control (RC) 16, a Clinician's Programmer (CP) 18, an External Trial Stimulator (ETS) 20, and an external charger 22.

The IPG 14 is physically connected via two lead extensions 24 to the stimulation leads 12, which carry a plurality of electrodes 26 arranged in an array. The IPG 14 includes a replenishable power source, telemetry circuitry, and pulse generation circuitry that delivers electrical stimulation energy in the form of a pulsed electrical waveform (i.e., a temporal series of electrical pulses) to the electrode array 26 in accordance with a set of stimulation parameters. The IPG 14 and stimulation leads 12 can be provided as an implantable neurostimulation kit, along with, e.g., a hollow needle, a stylet, a tunneling tool, and a tunneling straw. Further details discussing implantable kits are disclosed in U.S. Patent Publication 2009/0216306, entitled "Temporary Neurostimulation Lead Identification Device," which is expressly incorporated herein by reference.

The ETS 20 may also be physically connected via percutaneous lead extensions 28 or external cable 30 to the stimulation lead 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
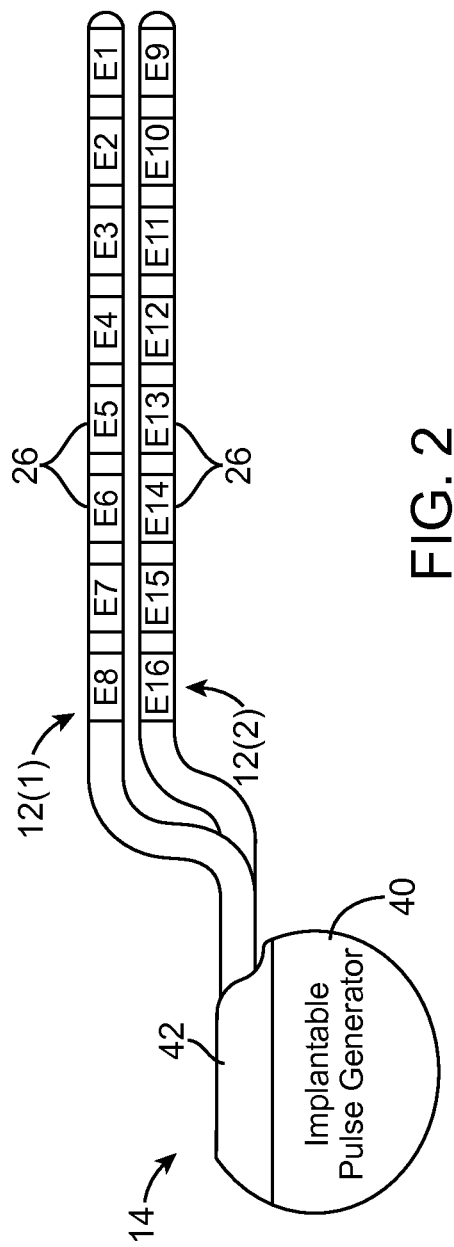
FIG. 2 is a plan view of an implantable pulse generator (IPG) and two neurostimulation leads used in the SCS system of FIG. 1.

Referring now to FIG. 2, the external features of the stimulation leads 12 and the IPG 14 will be briefly described. Each of the stimulation leads 12 has eight electrodes 26 (respectively labeled E1-E8 and E9-E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. Pat. No. 7,650,184, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes two ports (not shown) for receiving the proximal ends of the three percutaneous leads 12. In the case where the lead extensions 24 are used, the ports may instead receive the proximal ends of such lead extensions 24.

Figure 3:
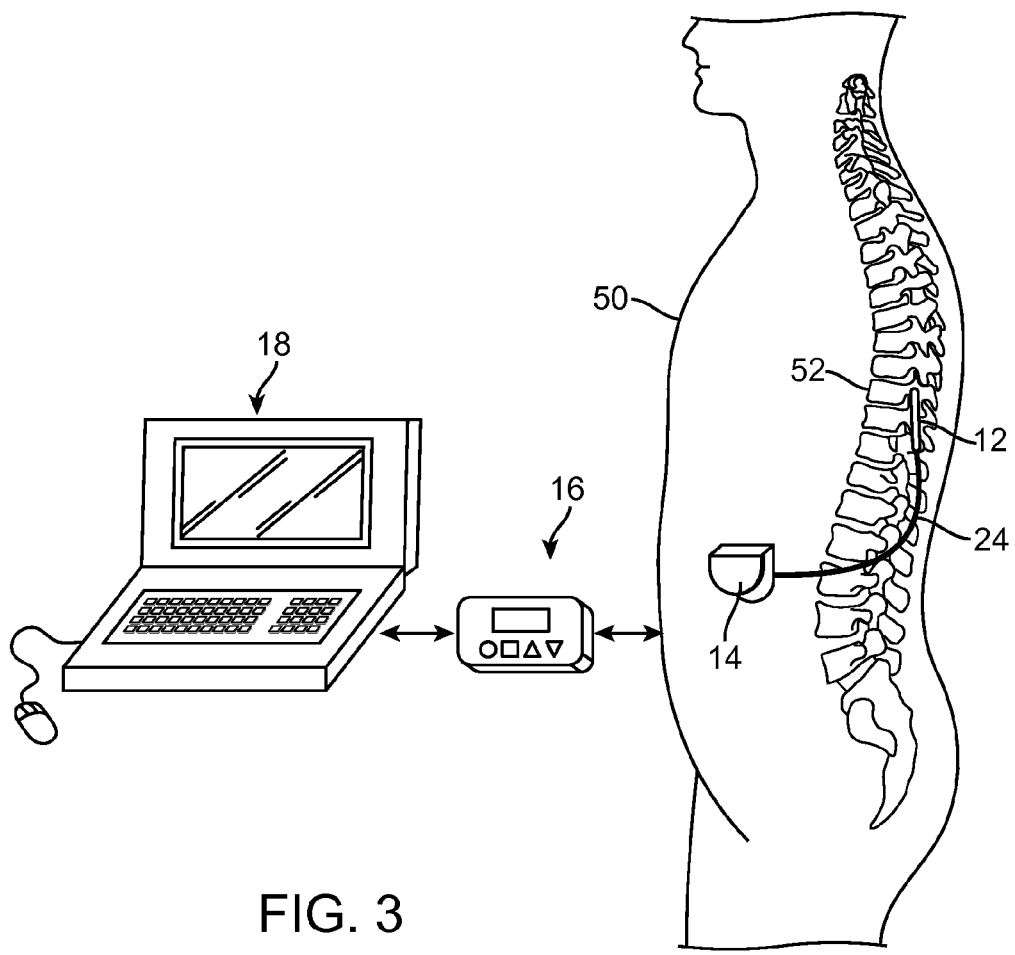
FIG. 3 is a plan view of the SCS system of FIG. 1 in use with a patient.

Referring to FIG. 3, the stimulation leads 12 are implanted within the spinal column 46 of a patient 48. The preferred placement of the stimulation leads 12 is adjacent, i.e., resting near, or upon the dura, adjacent to the spinal cord area to be stimulated. Due to the lack of space near the location where the stimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the stimulation leads 12. As there shown, the CP 18 communicates with the IPG 14 via the RC 16. While the stimulation leads 12 are illustrated as being implanted near the spinal cord area of a patient, the stimulation leads 12 may be implanted anywhere in the patient's body, including a peripheral region, such as a limb, or the brain. After implantation, the IPG 14 is used to provide the therapeutic stimulation under control of the patient.

Significantly, the neurostimulation system 10 provides the user status information with respect to the replenishable power source contained within the IPG 14 without requiring the user to initiate a programming session between the RC 16 and IPG 14. In performing this function, the IPG 14 is capable of broadcasting the status information to the RC 16 at regular intervals (e.g., once a day) or irregular intervals (e.g., when the stored energy in the power source falls below a threshold level). In the exemplary embodiment, the RC 16 need not continually remain on (i.e., in a relatively high energy consumption state) for it to receive the status information from the RC 16.

In particular, the IPG 14 is configured for monitoring a quantity of the stored energy in the replenishable power source, generating a battery charge status signal based on the monitored quantity of stored energy, and generating a battery charge status signal based on the quantity of stored energy. The battery charge status signal may be, e.g., an alert signal (meaning that it only indicates if a particular condition has been satisfied or not satisfied (e.g., the stored energy in the power source is below a threshold level) or a signal comprising quantitative information indicating the remaining energy level in the replenishable power source, which may be absolute (e.g., 10 Joules left) or relative (40% energy capacity left) or quantitative information indicating the remaining operating time of the replenishable power source (e.g., 6 hours left) or relative (50% operating time left). The IPG 14 is also configured for transcutaneously sending a communication initiation signal (e.g., a wake-up signal or an alert signal) and the battery charge status signal to the RC 16.

The RC 16 is configured for transcutaneously receiving the communication initiation signal from the IPG 14. If the communication initiation signal is a wake-up signal, the RC 16 will wake-up (change from a relatively low energy consumption state to a relatively high energy consumption state) and send an acknowledgment signal back to the IPG 14 indicating that it has received the wake-up signal. If the communication initiation signal is an alert signal, the RC 16, while already awoken, will send an acknowledgment signal back to the IPG 14 and listen for subsequent signals from the IPG 14, and in particular, the battery charge status signal. The RC 16 will then generate a user-discernible signal, which may be, e.g., an alert signal, such as beeping sound, or a signal that quantitatively indicates the remaining energy level in the replenishable power source or the remaining operating time of the replenishable power source.

Although the RC 16 is described as being the external device that generates the user-discernible signal in response to receiving the battery charge status signal from the IPG 14, other external devices, such as the charger 22, can alternatively or additionally perform this function.

Figure 4:
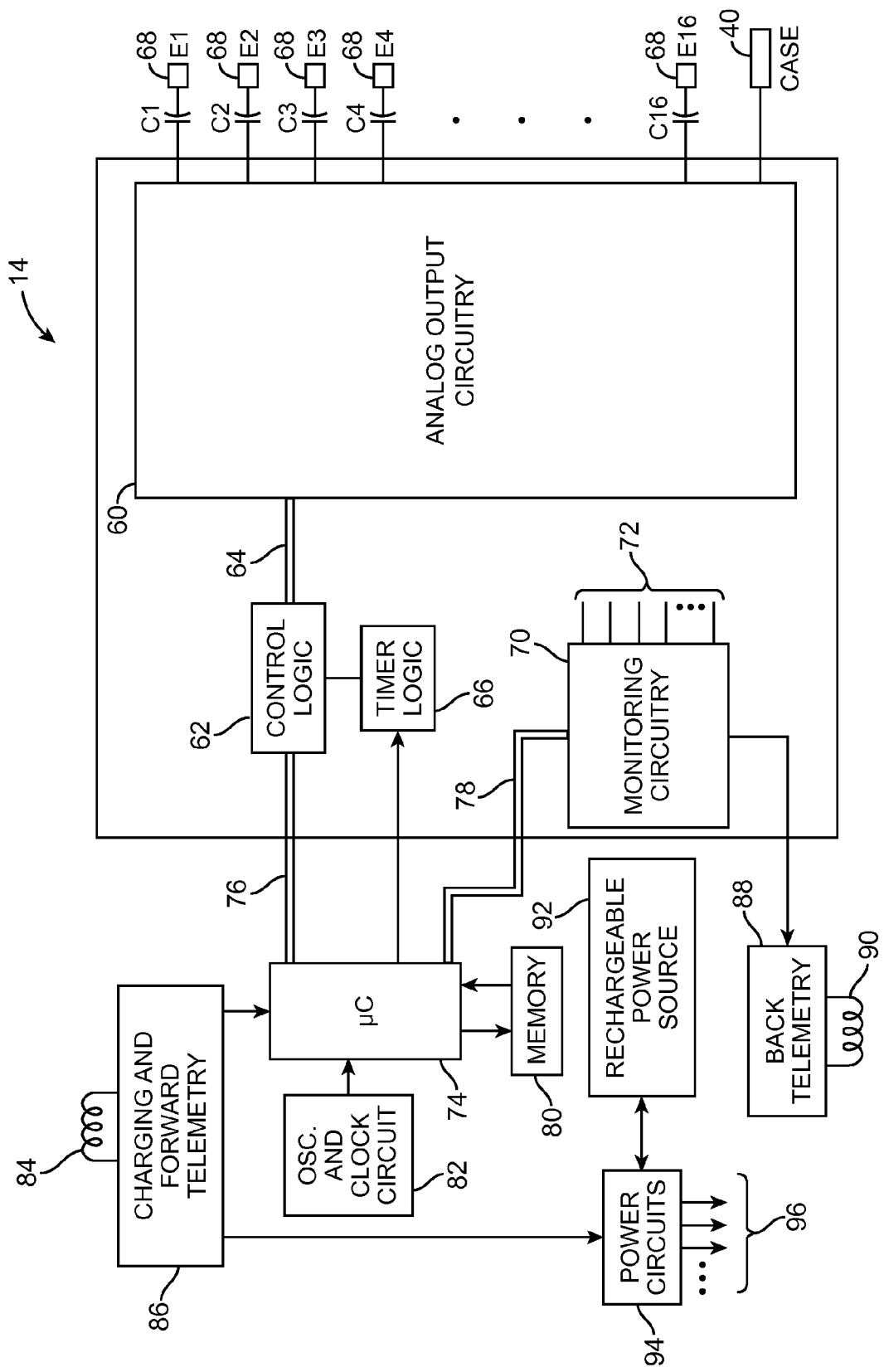
FIG. 4 is a block diagram of the internal components of the IPG of FIG. 1.

Turning next to FIG. 4, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 μs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., battery voltage, temperature, and the like. Significantly, monitored battery voltage allows the quantity of the stored energy in the battery (discussed below) to be determined, so that charge status information can be provided to the RC 16.

The IPG 14 further comprises processing circuitry in the form of a microcontroller 74 that controls the control logic 62 over data bus 76, and obtains status data from the monitoring circuitry 70 via data bus 78. The microcontroller 74 additionally controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided. Significantly, the microcontroller 74 is configured for generating a battery charge status signal (e.g., an alert signal or a signal comprising quantitative information indicating the remaining energy level in the replenishable power source and/or indicating the remaining operating time of the replenishable power source) based on the quantity of the stored energy in the battery monitored by the monitoring circuitry 70.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data (including the battery charge status signal) to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16. For the purpose of sending the battery charge status signal to the RC 16 without requiring the user to operate the RC 16, the back telemetry circuitry 88 is also configured for sending a communication initiation signal in the form of a wake-up signal to the RC 16 to wake-up the RC 16 (i.e., change the RC 16 from a relatively low energy consumption state to the relatively high energy consumption state) and an alert signal to the RC 16 to prompt the awoken RC 16 to receive the subsequent charge status signal.

The IPG 14 further comprises a replenishable power source 92, which may, e.g., comprise a rechargeable battery, such as a lithium-ion or lithium-ion polymer battery. The rechargeable battery 92 is recharged using rectified AC power (or DC power converted from AC power through other means, e.g., efficient AC-to-DC converter circuits) received by the AC receiving coil 84. To recharge the battery 92, the external charger 22, which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the battery 92.

The battery 92 may be chargeable to 80% of its capacity within about an hour, and is chargeable to its full capacity without about two hours. Moreover, at an 80% charge, a single battery discharge is able to support stimulation at typical stimulation parameter settings on one channel for approximately three weeks, and on four channels for approximately one week, after ten years of cycling. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

The IPG 14 further comprises power circuits 94 to which the rechargeable battery 92 provides an unregulated voltage. The power circuits 94, in turn, generate the various voltages 96, some of which are regulated and some of which are not, as needed by the various circuits located within the IPG 14 for providing the operating power to the IPG 14. The power circuits 94 also include protection circuitry that protects the rechargeable battery 92 from overcharging. Also, safeguarding features are incorporated that assure that the battery 92 is always operated in a safe mode upon approaching a charge depletion. Potentially endangering failure modes are avoided and prevented through appropriate logic control that is hardwired into the IPG 14, or otherwise set in the IPG 14 in such a way that the patient cannot override them.

Figure 5:
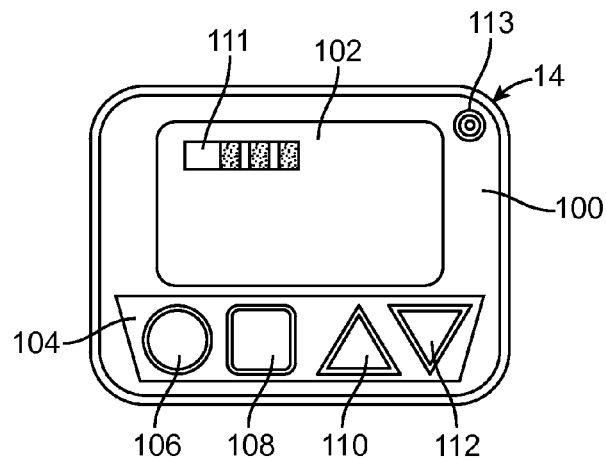
FIG. 5 is a plan view of a remote control that can be used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate. The display screen 102 includes a battery charge status icon 111 that shows the remaining energy level in the rechargeable battery 92 of the IPG 14. In the illustrated embodiment, the remaining energy level is displayed as being a relative measure (i.e., as a series of bars). Alternatively, the battery charge status icon 111 may show the remaining operating time of the replenishable power source. Preferably, an audio transducer 113 is used to alert the user with distinctive tones (e.g., with a series of beeps, music, or voice messages) in the case of a low-battery condition (i.e., if the quantity of the charge in the battery 92 of the IPG 14 is below a threshold level (e.g., below 10% of the total capacity of the battery 92)). Alternatively, the battery charge status icon 111 may flash (or otherwise changes in some fashion) in order to alert the user when a low battery condition occurs. Other types of indicators can be used to alert the user to a low battery condition. For example, the RC 16 may include a mechanical transducer that vibrates when a low battery condition occurs. Other battery status information, including when the battery 92 was last recharged, how long it was recharged and the number of times the battery 92

Figure 6:
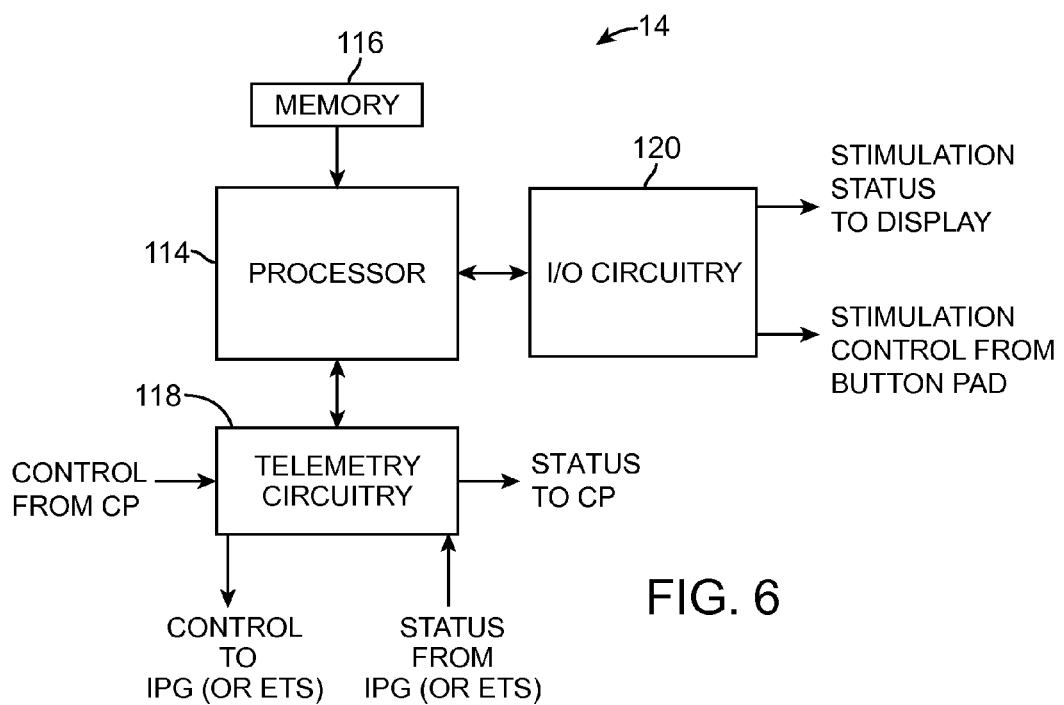
FIG. 6 is a block diagram of the internal componentry of the remote control of FIG. 5.

Referring to FIG. 6, the internal components of an exemplary RC 16 will now be described. The RC 16 generally includes a control circuitry 114 (e.g., a microcontroller), memory 116 that stores an operating program for execution by the control circuitry 114, and telemetry circuitry 118 for transmitting control data (including stimulation parameters and requests to provide status information) to the IPG 14 and receiving control signals (including the communication initiation signal) and status information (including the battery charge status signal) from the IPG 14 via link 34 (shown in FIG. 1), as well as receiving the control data from the CP 18 and transmitting the status data to the CP 18 via link 36 (shown in FIG. 1). The control circuitry 114 is configured for changing the RC 16 from a relatively low energy consumption state to a relatively high energy consumption state in response to the received communication initiation signal (e.g., the wake-up signal) via the telemetry circuitry 118. The RC 16 further includes input/output circuitry 120 for receiving stimulation control signals from the button pad 104 and transmitting status information to the display screen 102 (shown in FIG. 5). Further details of the functionality and internal componentry of the RC 16 are disclosed in U.S. Pat. No. 6,895,280, which has previously been incorporated herein by reference.

It should be appreciated that although the battery status signal has been described as a battery charge status signal for use with a rechargeable battery, the battery status signal may also indicate an end-of-life/end-of-service (EOL/EOS) condition with respect to a non-rechargeable battery. In this case, the battery status signal will notify the patient that the IPG 14 needs to be explanted from the patient and replaced with a new IPG 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable medical device, comprising:
a power source configured for storing energy;
monitoring circuitry configured for monitoring a quantity of the stored energy in the power source; and
control circuitry configured for generating a battery status signal based on the monitored quantity of stored energy;
telemetry circuitry configured for transcutaneously sending a communication initiation signal to an external device to initiate a communications link with the external device, and sending the battery status signal to the external device, wherein the communication initiation signal is sent prior to the battery status signal; and
a housing containing the power source, the monitoring circuitry, the control circuitry, and the telemetry circuitry.

2. The implantable medical device of claim 1, wherein the power source is a rechargeable battery, and the battery status signal is a battery charge status signal.

3. The implantable medical device of claim 1, wherein the power source is a non-rechargeable battery, and the battery status signal is a battery end-of-life/end-of-service (EOL/EOS) status signal.

4. The implantable medical device of claim 1, wherein the battery status signal is an alert signal that indicates that the stored energy in the power source is below a threshold level.

5. The implantable medical device of claim 1, wherein the battery status signal comprises quantitative information indicating the remaining energy level in the power source.

6. The implantable medical device of claim 1, wherein the battery status signal comprises quantitative information indicating the remaining operating time of the power source.

7. The implantable medical device of claim 1, wherein the communication initiation signal is a wake-up signal capable of prompting the external control device to change from a first energy consumption state to a second energy consumption state higher than the first energy consumption state.

8. An external device for use with a rechargeable implantable medical device having a power source, comprising:
telemetry circuitry configured for transcutaneously receiving a communication initiation signal, and a battery status signal from the rechargeable implantable medical device, wherein the communication initiation signal initiates a communications link with the external device prior to receiving the battery status signal;

control circuitry configured for changing the external device from a first energy consumption state to a second energy consumption state higher than the first energy consumption state in response to the received communication initiation signal; and an indicator configured for generating a user-discernible signal in response to the received status signal.

9. The external device of claim 8, wherein the indicator is an audio transducer.

10. The external device of claim 8, wherein the indicator is a visual display.

11. The external device of claim 8, wherein the user-discernible signal is an alert signal.

12. The external device of claim 8, wherein the user-discernible signal quantitatively indicates the remaining energy level in the power source.

13. The external device of claim 8, wherein the user-discernible signal quantitatively indicates the remaining operating time of the power source.

14. A medical system, comprising:

an implantable medical device having a power source, the implantable medical device configured for monitoring a quantity of the stored energy in the power source, generating a battery status signal based on the monitored quantity of stored energy, and for transcutaneously transmitting a communication initiation signal and the battery status signal; and an external device configured for transcutaneously receiving the communication initiation signal and the battery status signal from the rechargeable implantable medical device, changing from a first energy consumption state to a second energy consumption state higher than the first energy consumption state in response to the received communication initiation signal, and for generating a user-discernible signal in response to the received status signal, wherein the communication initiation signal initiates a communications link between the external device and the implantable medical device prior to receiving the battery status signal.

15. The medical system of claim 14, wherein the power source is a rechargeable battery, and the battery status signal is a battery charge status signal.

16. The medical system of claim 14, wherein the power source is non-rechargeable battery, and the battery status signal is a battery end-of-life/end-of-service (EOL/EOS) status signal.

17. The medical system of claim 14, wherein the battery status signal indicates that the stored energy in the power source is below a threshold level, and the user-discernible signal is an alert signal.

18. The medical system of claim 14, wherein the battery status signal comprises quantitative information indicating the remaining energy level in the power source, and the user-discernible signal quantitatively indicates the remaining energy level in the power source.

19. The medical system of claim 14, wherein the battery status signal comprises quantitative information indicating the remaining operating time of the power source, and the user-discernible signal quantitatively indicates the remaining operating time of the power source.

20. The medical system of claim 14, wherein the implantable medical device is an implantable pulse generator.

* * * * *